United States Patent [19]  
Sato et al.

[11] Patent Number: 4,728,659  
[45] Date of Patent: Mar. 1, 1988

[54] AMINOMETHYL DERIVATIVES AND PREPARATION PROCESS THEREOF AS WELL AS PLATELET AGGREGATION INHIBITORS CONTAINING SAME

[75] Inventors: Susumu Sato, Chiba; Tadayuki Kouda, Narita; Tatsuhiko Katori, Ibaragi, all of Japan

[73] Assignee: SS Pharmaceutical Co., Ltd., Tokyo, Japan

[21] Appl. No.: 748,686

[22] Filed: Jun. 25, 1985

[30] Foreign Application Priority Data

Jun. 27, 1984 [JP] Japan ................. 59-132707  
Jun. 27, 1984 [JP] Japan ................. 59-132708  
Sep. 25, 1984 [JP] Japan ................. 59-200190

[51] Int. Cl.$^4$ ............... C07D 213/80; A61K 31/455  
[52] U.S. Cl. .................... 514/356; 546/322; 564/342; 564/344; 564/345  
[58] Field of Search ............... 546/322; 514/356

[56] References Cited  
U.S. PATENT DOCUMENTS 2,539,801 1/1951 Van Hook et al. ............... 544/175

OTHER PUBLICATIONS

Chemical Abstracts, vol. 68, No. 16, Apr. 15, 1968, p. 7482, No. 77634w, Columbus, Ohio, US; N. M. Libman et al.: "Amino Alcohols of the Acetrylenic Series. VI." & Zh. Org. Khim. 4(1), 20-5 (1968).

Chemical Abstracts, vol. 84, No. 7, Feb. 16, 1976, p. 445, No. 43543f, Columbus, Ohio, US; L. I. Vereshchagin et al.: "Addition of Alcohols and Amines to Acetylenic Amino- and Brokomoketones" & Zh. Org. Khim. 1975, 11(11), 2311-15.

Primary Examiner—Alan L. Rotman  
Assistant Examiner—Dale A. Bjorkman  
Attorney, Agent, or Firm—Oblon, Fisher, Spivak, McClelland & Maier

[57] ABSTRACT

Disclosed herein are aminomethyl derivatives each of which is of the following general formula (I):

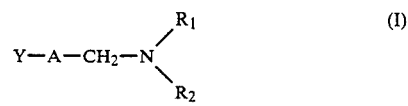

wherein A represents a group —C≡C— or —CH=CH—, Y represents a group

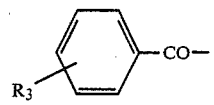

(in which $R_3$ being a lower alkyl or alkoxy group or a halogen atom) or

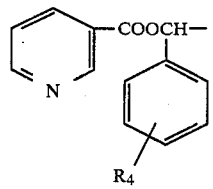

(in which $R_4$ being a hydrogen atom or $R_3$), and $R_1$ and $R_2$ represent individually a lower alkyl group, with a proviso that Y is other than the group

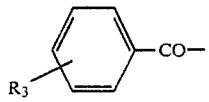

when A means the group —CH=CH—, their preparation process and platelet aggregation inhibitors containing same.

4 Claims, No Drawings

AMINOMETHYL DERIVATIVES AND PREPARATION PROCESS THEREOF AS WELL AS PLATELET AGGREGATION INHIBITORS CONTAINING SAME

This invention relates to novel aminomethyl derivatives, and more specifically to aminomethyl derivatives having strong platelet aggregation inhibitory effects and their acid addition salts, and preparation process thereof as well as platelet aggregation inhibitors containing same.

The present inventors have synthesized a variety of compounds and investigated their pharmacological effects. In the course of the investigation, it has been found that certain specific aminomethyl derivatives have excellent platelet aggregation inhibitory effects and are hence useful for thrombus-inducing diseases of circulatory organs, leading to completion of this invention.

Accordingly, the first object of this invention is to provide an aminomethyl derivative of the following general formula (I):

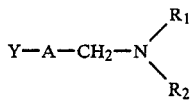

wherein A represents a group $-C\equiv C-$ or $-CH=CH-$, Y represents a group

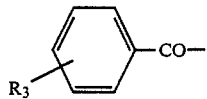

(in which $R_3$ being a lower alkyl or alkoxy group or a halogen atom) or

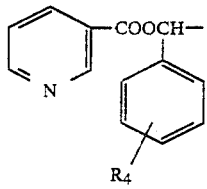

(in which $R_4$ being a hydrogen atom or $R_3$), and $R_1$ and $R_2$ represent individually a lower alkyl group, with a proviso that Y is other than the group

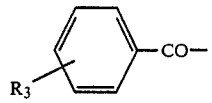

when A means the group $-CH=CH-$.

The second object of this invention is to provide a process for preparing the aminomethyl derivative represented by the general formula (I).

Furthermore, the third object of this invention is to provide a platelet aggregation inhibitor comprising the aminomethyl derivative.

The novel aminomethyl derivatives (I) of this invention may be divided roughly into the following two groups of compounds (Ia) and (Ib):

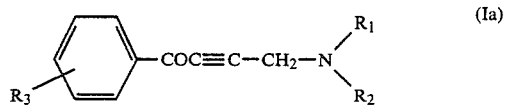

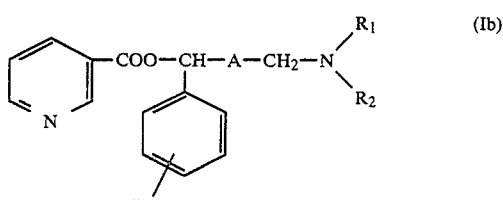

wherein A, $R_1$, $R_2$, $R_3$ and $R_4$ have the same meanings as defined above.

Of these, the compounds of the formula (Ia) are derivatives of the so-called butynophenone. Reported earlier work on such butynophenone derivatives is limited to compounds of the above general formula (I) in which $R_3$ is a hydrogen atom and $R_1$ and $R_2$ mean individually an ethyl group [Zh. Org. Khim. 11, 2311–5 (1975)]. However, their pharmacological effects have not been known to all to date.

The compounds represented by the general formula (Ia) may, for example, be prepared in accordance with the below-described reaction scheme. Incidentally, it is also possible to prepare, in the same manner, the above-mentioned compounds of the general formula (Ia) in which $R_3$ represents a hydrogen atom and $R_1$ and $R_2$ represents individually a lower alkyl group which may include an ethyl group.

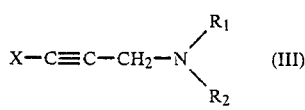

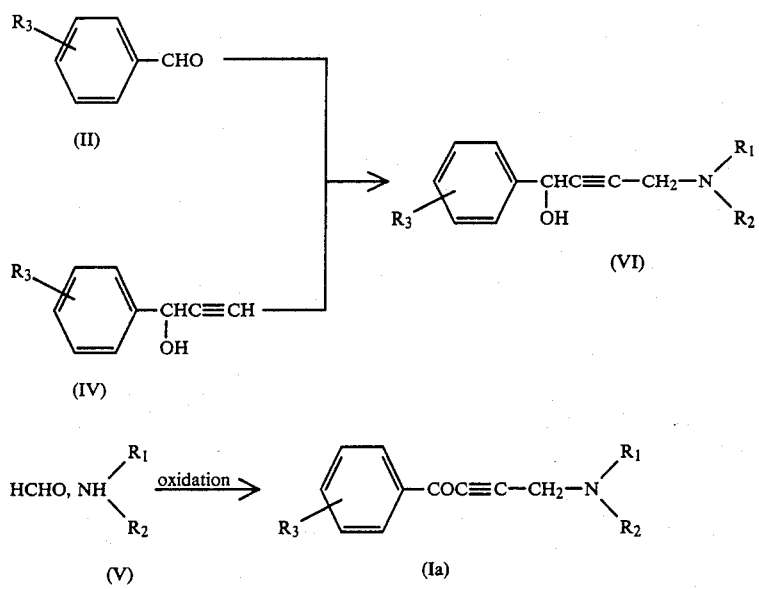

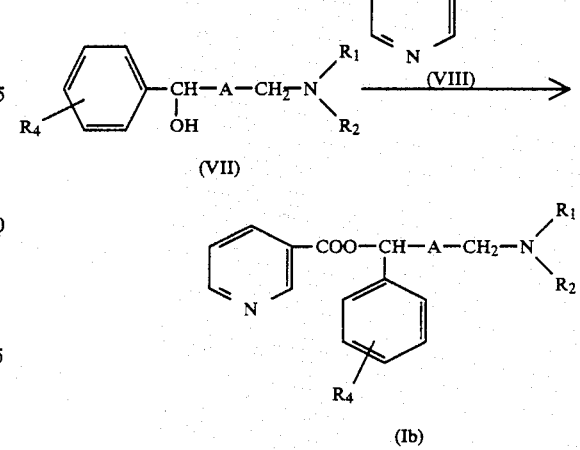

wherein X represents a magnesium halide or alkali metal, and $R_1$, $R_2$ and $R_3$ have the same meaning as defined above.

Namely, the intended aminomethyl derivative (Ia) is prepared by reacting a benzaldehyde derivative represented by the general formula (II) with a metal compound of propargyl amine derivative represented by the general formula (III) or reacting an α-phenyl propargyl alcohol derivativere presented by the general formula (IV) with formaldehyde and a secondary amine derivative represented by the general formula (V) to obtain an alkynolamine derivative represented by the general formula (VI) and then oxidizing the alkynol amine derivative with an oxidizing agent such as manganese dioxide or the like.

The reaction for obtaining the compound (VI) from the compound (II) and the compound (III) may be practiced by stirring, at room temperature, the compound (II) and compound (III) or causing them to reflux for several hours in a solvent inert to the reaction. As the solvent, ether, tetrahydrofuran or the like may be employed.

On the other hand, the reaction for obtaining the compound (VI) from the compound (IV), formaldehyde and the compound (V) is the so-called Mannich reaction. This reaction may be practiced by mixing the above starting raw materials and then stirring the resultant mixture for several hours in the range of from room temperature to 60°–70° C. As a solvent for the reaction, may be employed water, methanol, ethanol, dioxane or the like.

The thus-obtained compound (VI) is further subjected to an oxidation reaction, thereby obtaining the intended compound (Ia). The oxidation may be effected by a method known per se in the art. For example, it may be effected by adding the compound (VI) and an oxidizing agent such as manganese dioxide or the like to a solvent inert to the reaction, such as methylene chloride, chloroform, carbon tetrachloride, acetone, benzene or the like and then mixing them at room temperature for several hours.

Turning to the compounds represented by the formula (Ib), they may be prepared, for example, in accordance with the following reaction equation:

wherein $R_1$, $R_2$, $R_4$ and A have the same meaning as defined above. Namely, the intended aminomethyl derivative (Ib) may be prepared by reacting an alkynolamine or alkenolamine represented by the general formula (VII) with nicotinic acid (VIII) or its reactive derivative.

As the reactive derivative of nicotinic acid (VIII), may be mentioned for example an acid halogenide, acid anhydride, mixed acid anhydride, ester or the like. When such a reactive derivative of nicotinic acid (VIII) is used, it is preferred to conduct the reaction in the presence of pyridine, a tertiary amine such as trimethylamine or triethylamine, or an deoxidizer such as potassium carbonate, sodium carbonate, potassium hydrogencarbonate, sodium hydrogencarbonate, potassium hydroxide or sodium hydroxide. This reaction may be practiced by stirring, at room temperature, the reactants or causing them to reflux for several hours in a suitable solvent, for example in a solvent inert to the reaction such as tetrahydrofuran, benzene, toluene, acetone or methyl ethyl ketone. When the alkanolamine or alkenolamine represented by the general formula (VII) is reacted directly with nicotinic acid (VIII), it is preferred to use a condensing agent. For example, it is preferred to conduct the reaction in the presence of a 2-halo-1-alkylpyridinium salt and pyridine or a tertiary amine such as triethylamine or tributylamine, or in the presence of diethyl azodicarboxylate and triphenylphosphine as condensing agents. It is preferred to conduct this reaction in a solvent inert to the reaction. As such a solvent, may be mentioned ether, tetrahydrofuran, benzene, toluene, acetonitrile, chloroform, dichloromethane, or the like.

The thus-obtained aminomethyl derivative (I) of this invention may be converted, if necessary, into an inorganic salt such as hydrochloride, hydrobromide or sulfate or an organic salt such as maleate, fumarate, tartrate, citrate or methanesulfonate.

By the way, when A means a group —CH=CH— in the compound (I) of this invention, the compound (I) contains both cis- and trans-isomers. Both of these isomers are included in the present invention.

The platelet aggregation inhibitory effects of the thus-obtained compounds of this invention were tested. Test results are as follows:

Platelet Aggregation Inhibitory Effects 1:

Blood, which had been added with sodium citrate, was collected from a male rabbit (body weight: 3 Kg), which was then subjected suitably to centrifugation so that platelet-rich plasma (PRP) and platelet-poor plasma (PPP) were obtained. Inhibitory effects of certain sample compounds of this invention against aggregation by ADP (3 μM) and arachidonic acid (1 mM) were thereafter tested by a method known per se in the art. Each sample compound was dissolved in 5% dimethylsulfoxide (DMSO) and Tween 80 (trade mark) and was then added to PRP 2 minutes before addition of each of the aggregation agents to the PRP.

Test results are shown in Table 1.

TABLE 1

| 50% Platelet Aggregation Inhibitory Concentration ($IC_{50}$) [μg/ml] | | | | |
|---|---|---|---|---|
| Sample compound of formula (Ia) | | | Platelet aggregation agent | |
| $R_3$ | $R_1$ | $R_2$ | ADP | Arachidonic acid |
| 4-$CH_3$ | $C_2H_5$ | $C_2H_5$ | 7.0 | 2.5 |
| 4-$OCH_3$ | $C_2H_5$ | $C_2H_5$ | 9.0 | 3.6 |
| — | $CH_3$ | $CH_3$ | 21.0 | 4.7 |
| — | $C_2H_5$ | $C_2H_5$ | 20.0 | 4.5 |
| — | $C_2H_5$ | $C_3H_7$ | 18.0 | 4.3 |

As apparent from Table 1, the compounds of this invention exhibited strong inhibitory effects against aggregation of platelets by ADP and against aggregation of platelets by arachidonic acid.

Platelet Aggregation Inhibitory Effects 2:

Each sample compound was orally administered at 30 mg/Kg to a male Wister rat (body weight: 220 g) which had fasted for 24 hours. Platelet-rich plasma was obtained from blood which had been collected 2 hours after the administration and added with sodium citrate. Changes in platelet aggregation upon addition of 60 μM of ADP or 100 μg/ml of collagen were observed. The number of platelets was adjusted to $6 \times 10^5$ platelets/$mm^3$ for aggregation by ADP and to $3 \times 10^5$ platelets/$mm^3$ for aggregation by collagen. Each of the sample compounds was dissolved in DMSO+Tween 80 (trade mark) prior to its administration. Test results are given in Table 2.

TABLE 2

| Sample compounds of formula (Ib) | | | | Percent inhibition against aggregation ADP | Percent inhibition against aggregation collagen |
|---|---|---|---|---|---|
| $R_4$ | $R_1$ | $R_2$ | A | | |
| 4-$CH_3$ | $C_2H_5$ | $C_2H_5$ | —C≡C— | 20.1 | 37.6 |
| 4-$CH_3$ | $C_2H_5$ | $C_2H_5$ | —CH=CH— (trans) | 30.5 | 31.5 |

As clearly envisaged form Table 2, the compounds of this invention showed strong inhibitory effects against aggregation of platelets by ADP and against aggregation of platelets by collagen.

Acute Toxicity:

Each of certain sample compounds (which had been obtained in Examples 6, 7, 10 and 15–17, which will be given herein) was dissolved in water and was then administered intraperitoneally at a dose of 200 mg/Kg to a group of five ddY male mice. Those mice were fed for 7 days while observing them. Even after the elapsed time of 7 days, all the mice were still alive and no abnormality was observed thereon. Therefore, the $LD_{50}$ of each of the sample compounds is greater than 200 mg/Kg.

The aminomethyl derivatives (I) of this invention may be administered either orally or parenterally. The platelet aggregation inhibitors of this invention may be formed into various preparation forms depending on their ways of administration, for example, into orally-dosable preparation forms such as powders, tablets, capsules, granules, liquid preparations and the like; and parenterally-dosable preparation forms such as subcutaneously-injectable solutions, intramuscularly-injectable solutions and intravenously-injectable solutions, preparations suitable for admixture with transfusional solutions, ointments, tinctures, plasters, suppositories, etc.

The above formation into dosable preparation forms may be carried out by methods known per se in the art. Namely, the aminomethyl derivatives (I) may be combined and processed suitably with an excipient such as starch, lactose, mannitol or the like; a binder such as sodium carboxymethyl cellulose, hydroxypropyl cellulose or the like; a disintegrator such as crystalline cellulose, calcium carboxymethyl cellulose or the like; a lubricant such as talc, magnesium stearate or the like; a fluidity improver such as light silicic anhydride; and/or the like, thereby to produce powders, tablets, capsules or granules.

Making use of the fact that salts of the aminomethyl derivatives (I) of this invention, for example, their hydrochlorides are soluble in aqueous solvents such as water, physiological saline and the like, it is possible to produce aqueous liquid preparations, injectable aqueous preparations, etc.

For the preparation of suppositories, it is necessary to disperse the aminomethyl derivatives (I) in a usual base material, for example, cacao butter, synthetic oil and fat or the like and then to solidify the resultant dispersion.

Although subject to variations depending on the seriousness of diseases, the thus-prepared platelet aggregation inhibitors of this invention may be administered to adults, generally, at daily doses of 0.02–100 mg/Kg in terms of their aminomethyl derivatives (I) when administered orally or at doses of 0.01–50 mg/Kg in terms of their aminomethyl derivatives (I) when administered perenterally. It is suitable to administer these doses by dividing them into 1 to several portions a day.

EFFECTS OF THE INVENTION

Since the aminomethyl derivatives (I) of this invention have excellent platelet aggregation inhibitory effects and their safety levels are also high, they are effective, as platelet aggregation inhibitors, for the treatment and prevention of various diseases induced by the formation of thrombi, for example, venous thrombosis, coronary thrombosis in cardiac infarction, pulmonary embolism, cerebral thrombosis and embolism, etc.

The present invention will hereinafter be described further by the following Examples.

EXAMPLE 1

N-[4-(p-Methylphenyl)-4-oxo-2-butynyl]-N,N-diethylamine

Dissolved in 35 ml of chloroform was 0.58 g of N-[4-(p-methylphenyl)-4-hydroxy-2-butynyl]-N,N-diethylamine. After adding 6.52 g of manganese dioxide with ice-cooling and stirring, the resultant mixture was stirred at room temperature for 3 hours. The resultant inorganic matter was filtered off and the solvent was distilled off under reduced pressure to obtain 0.53 g of the intended product as a light yellowish oily substance (yield: 92.5%).

NMR δppm (CDCl$_3$): 8.0(d, 2H), 7.25(d, 2H), 3.7(s, 2H), 2.7(q, 4H), 2.4(s, 3H), 1.1(t, 6H).

IR $\nu_{max}^{neat}$ cm$^{-1}$: 2230, 1645.

The above oily substance was dissolved in anhydrous ether, to which HCl-containing ethanol was added dropwise with ice-cooling. Deposited hydrochloride salt of the title compound consisting of light yellowish crystals was collected.

Melting point: 115°–117° C.

EXAMPLES 2-5

Compounds given in Table 3 were obtained in the same manner as in Example 1.

TABLE 3

| | Formula (Ia) | | | | | m.p. (°C.) |
|---|---|---|---|---|---|---|
| Example | R$_3$ | R$_1$ | R$_2$ | NMR δ ppm (CDCl$_3$) | IR$\nu_{max}^{neat}$cm$^{-1}$ | (—HCl) |
| 1 | 4-CH$_3$ | C$_2$H$_5$ | C$_2$H$_5$ | 8.0 (d,2H), 7.25 (d,2H), 3.7 (s,2H), 2.7 (q,4H), 2.4 (s,3H), 1.1 (t,6H) | 2230, 1645 | 115–117 |
| 2 | 4-C$_2$H$_5$ | C$_2$H$_5$ | C$_2$H$_5$ | 8.0 (d,2H), 7.25 (d,2H), 3.7 (s,2H), 2.0–3.0 (m,6H), 1.25 (t,3H), 1.1 (t,6H) | 2240, 1640 | 107–109 |
| 3 | 4-i-C$_3$H$_7$ | C$_2$H$_5$ | C$_2$H$_5$ | 8.0 (d,2H), 7.25 (d,2H), 3.7 (s,2H), 2.4–3.1 (m,5H), 0.9–1.5 (m,12H) | 2240, 1640 | 92–94 |
| 4 | 4-CH$_3$O | C$_2$H$_5$ | C$_2$H$_5$ | 8.0 (d,2H), 6.85 (d,2H), 3.8 (s,3H), 3.65 (s,2H), 2.7 (q,4H), 1.1 (t,6H) | 2240, 1650 | 128–130 |
| 5 | 4-Cl | C$_2$H$_5$ | C$_2$H$_5$ | 8.0 (d,2H), 7.4 (d,2H), 3.7 (s,2H), 2.65 (q,4H), 1.1 (t,6H) | 2230, 1640 | 95–97 |

EXAMPLE 6

N-(4-Nicotinoyloxy-4-phenyl-2-butynyl)-N,N-diethylamine

Dissolved in anhydrous tetrahydrofuran was 2.17 g of N-(4-phenyl-4-hydroxy-2-butynyl)-N,N-diethylamine, followed by an addition of 4 ml of pyridine. Then, 1.78 g of nicotinyl chloride hydrochloride was added at room temperature little by little. The resultant mixture was thereafter reacted at the same temperature for 4 hours. After the reaction, the solvent was distilled off under reduced pressure and the residue was taken up in chloroform. The resultant chloroform solution was washed with water and was then dried over anhydrous sodium sulfate. The chloroform was distilled off under reduced pressure and the residue was purified by column chromatography (silica gel) to obtain 1.5 g of the intended product as a light yellowish oily substance (yield: 46.6%).

Elemental analysis: Calculated for C$_{20}$H$_{22}$N$_2$O$_2$: C, 74.51; H, 6.88; N, 8.69. Found: C, 74.58; H, 6.92; N, 8.59.

EXAMPLES 7-14

Compound Nos. 7-14 given in Table 4 were obtained in the same manner as in Example 6.

TABLE 4

| | Formula (Ib) | | | | | |
|---|---|---|---|---|---|---|
| Example | R$_4$ | R$_1$ | R$_2$ | A | NMR δ ppm (CDCl$_3$) | Appearance |
| 6 | H | C$_2$H$_5$ | C$_2$H$_5$ | —C≡C— | 9.1 (d,1H), 8.6 (d.d,1H), 8.2 (m,1H), 7.1–7.7 (m,6H), 6.6 (m,1H), 3.5 (m,2H), 2.6 (q,4H), 1.05 (t,6H) | Light yellowish oily substance |
| 7 | p-CH$_3$ | C$_2$H$_5$ | C$_2$H$_5$ | —C≡C— | 9.15 (d,1H), 8.7 (d.d,1H), 8.2 (m,1H), 7.4 (d,2H), 7.3 (m,1H), 7.2 (d,2H), 6.7 (m,1H), 3.5 (m,1H), 2.55 (q,4H), 2.3 (s,3H), 1.05 (t,6H) | Light yellowish crystals (m.p. 54–56° C.) |
| 8 | p-C$_2$H$_5$ | C$_2$H$_5$ | C$_2$H$_5$ | —C≡C— | 9.31 (d,1H), 8.83 (d.d,1H), 8.38 (m,1H), 7.63 (d,2H), 7.33 (d,2H), 7.28 (m,1H), 6.80 (m,1H), 3.58 (m,2H), 2.60 (q,6H) 1.25 (t,3H), 1.08 (t,6H) | Light yellowish oily substance |
| 9 | p-C$_3$H$_7$-i | C$_2$H$_5$ | C$_2$H$_5$ | —C≡C— | 9.1 (d,1H), 8.62 (d.d,1H), 8.18 (m,1H), 7.47 (d,2H), 7.31 (m,1H), 7.21 (d,2H), 6.70 (m,1H), 3.5 (m,2H), 2.4–3.2 (m,1H), 2.55 (q,4H), 1.25 (d,6H), 1.04 (t,6H) | Light yellowish oily substance |
| 10 | p-OCH$_3$ | C$_2$H$_5$ | C$_2$H$_5$ | —C≡C— | 9.2 (d,1H), 8.7 (d.d,1H), | Light yellowish |

TABLE 4-continued

| Example | Formula (Ib) R4 | R1 | R2 | A | NMR δ ppm (CDCl3) | Appearance |
|---------|-----|-----|-----|-----|-----|-----|
|  |  |  |  |  | 8.2 (m,1H), 7.4 (d,2H), 7.3 (m,1H), 6.9 (d,1H), 6.7 (m,1H), 3.8 (s,3H), 3.5 (m,2H), 2.6 (q,6H), 1.05 (t,6H) | oily substance |
| 11 | p-Cl | C2H5 | C2H5 | —C≡C— | 9.2 (d,1H), 8.6 (d.d,1H), 8.2 (m,1H), 7.0–7.6 (m,5H), 6.7 (m,1H), 3.5 (m,2H), 2.6 (q,4H), 1.05 (t,6H) | Light yellowish oily substance |
| 12 | H | C2H5 | C2H5 | —CH=CH— (trans) | 9.2 (d,1H), 8.7 (d.d,1H), 8.3 (m,1H), 7.0–7.6 (m,6H), 6.5 (m,1H), 5.9 (m,2H), 3.1 (m,2H), 2.5 (q,4H), 1.0 (t,6H) | Light yellowish oily substance |
| 13 | p-CH3 | C2H5 | C2H5 | —CH=CH— (trans) | 9.2 (d,1H), 8.7 (d.d,1H), 8.3 (m,1H), 7.0–7.6 (m,5H), 6.5 (m,1H), 5.9 (m,2H), 3.1 (m,2H), 2.5 (q,4H), 2.3 (s,3H), 1.0 (t,6H) | Light yellowish oily substance |
| 14 | p-Cl | C2H5 | C2H5 | —CH=CH— (trans) | 9.2 (d,1H), 8.7 (d.d,1H), 8.3 (m,1H) 7.0–7.6 (m,5H), 6.5 (m,1H), 5.9 (m,2H), 3.1 (m,2H), 2.5 (q,4H), 1.0 (t,6H) | Light yellowish oily substance |

EXAMPLE 15

N-(4-Phenyl-4-oxo-2-butynyl)-N,N-dimethylamine

Dissolved in 50 ml of chloroform was 1.13 g of N-(4-phenyl-4-hydroxy-2-butynyl)-N,N-dimethylamine. After adding with ice-cooling and stirring 18 g of manganese dioxide to the resultant solution, the mixture was stirred at room temperature for 3 hours. After filtering off the resultant inorganic matter, the solvent was distilled off under reduced pressure to obtain 1 g of the intended product as a light yellowish oily substance (yield: 89.1%).

The above oily substance was dissolved in anhydrous ether, to which HCl-containing ethanol was added dropwise with ice-cooling and stirring. Deposited hydrochloride salt of the title compound was collected as light yellowish crystals by filtration.

Melting point: 102°–103° C.

EXAMPLE 16

N-(4-Phenyl-4-oxo-2-butynyl)-N-ethyl-N-n-propylamine

Dissolved in 100 ml of chloroform was 2.32 g of N-(4-phenyl-4-hydroxy-2-butynyl)-N-ethyl-N-n-propylamine. After adding with ice-cooling and stirring 25 g of manganese dioxide to the resultant solution, the mixture was stirred at room temperature for 5 hours. After filtering off the resultant inorganic matter, the solvent was distilled off under reduced pressure to obtain 1.8 g of the intended product as a light yellowish oily substance (yield: 78.6%).

The above oily substance was dissolved in anhydrous ether, to which HCl-containing ethanol was added dropwise with ice-cooling and stirring to obtain the hydrochloride salt of the title compound as light yellowish crystals.

Melting point: 103°–105° C.

EXAMPLE 17

Following the procedure of Example 15 or 16, were obtained compounds shown in Table 5.

TABLE 5

| Example | Formula (Ia) R3 | R1 | R2 | NMR δ ppm | IR $\nu_{max}^{neat}$ cm$^{-1}$ | m.p. (°C.) (—HCl) |
|---------|-----|-----|-----|-----|-----|-----|
| 15 | — | CH3 | CH3 | 8.0–8.3 (m,2H), 7.2–7.7 (m,3H), 3.5 (s,2H), 2.4 (s,6H) | 2240, 1640 | 102–103 |
| 17 | — | C2H5 | C2H5 | 8.0–8.3 (m,2H), 7.2–7.7 (m,3H), 3.7 (s,2H), 2.7 (q,4H), 1.1 (t,6H) | 2240, 1640 | 131–132 |
| 16 | — | C2H5 | C3H7 | 8.0–8.3 (m,2H), 7.2–7.7 (m,3H), 3.7 (s,2H), 2.4–2.9 (m,4H), 1.2–2.0 (m,2H), 1.1 (t,3H), 0.9 (t,3H) | 2240, 1640 | 103–105 |

EXAMPLE 18

(Tablet)

In a manner known per se in the art, a tablet of the following compositions (1) and (2) were prepared.

| (1) Aminomethyl derivative (obtained in Example 16) | 20 mg |
|---|---|
| Light silicic anhydride | 20 mg |
| Crystalline cellulose | 10 mg |
| Hydroxypropyl cellulose | 5 mg |
| Calcium carboxymethyl cellulose | 10 mg |
| Talc | 2 mg |
| Magnesium stearate | 1 mg |

The total weight was adjusted to 200 mg with lactose.

| (2) Aminomethyl derivative (obtained in Example 7) | 25 mg |
|---|---|
| Light silicic anhydride | 20 mg |
| Crystalline cellulose | 10 mg |
| Hydroxypropyl cellulose | 5 mg |
| Calcium carboxymethyl cellulose | 10 mg |
| Talc | 2 mg |
| Magnesium Stearate | 1 mg |

The total weight was adjusted to 205 mg with lactose.

EXAMPLE 19

(Injectable Preparation)

In a manner known per se in the art, an injectable preparation was produced with the following composition.

| Aminomethyl derivative (obtained in Example 16) | 20 mg |
| Physiological saline | balance to 2 ml |

EXAMPLE 20

(Capsule)

In a manner known per se in the art, granules of the following composition were prepared and they were filled in a capsule.

| Aminomethyl derivative (obtained in Example 1) | 20 mg |
| Light silicic anhydride | 17 mg |
| Crystalline cellulose | 7 mg |
| Magnesium stearate | 1 mg |

Total weight was adjusted to 180 mg with lactose.

EXAMPLE 21

(Suppository)

In a manner known per se in the art, a suppository of the following composition was prepared.

| Aminomethyl derivative (obtained in Example 7) | 20 mg |
| Cacao butter | 1180 mg |
| Total amount | 1200 mg |

We claim:

1. An aminomethyl derivative of the formula:

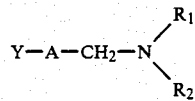

wherein A is selected from the group consisting of —C≡C— and —CH=CH—, Y is the group

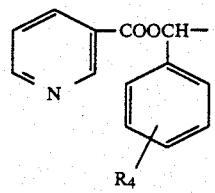

wherein $R_4$ is a hydrogen atom, a halogen atom, a lower alkyl or alkoxy group, and $R_1$ and $R_2$ are, individually, a lower alkyl group.

2. A platelet aggregation inhibitor comprising an effective amount of an aminomethyl derivative of the formula:

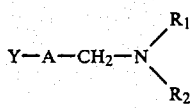

wherein A is selected from the group consisting of —C≡C— and —CH=CH—, Y is the group

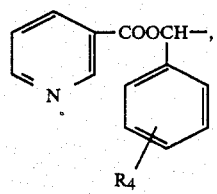

wherein $R_4$ is a hydrogen atom, a halogen atom, a lower alkyl or alkoxy group, and $R_1$ and $R_2$ are, individually, a lower alkyl group; and a pharmaceutically acceptable carrier or excipient.

3. A platelet aggregation inhibitor according to claim 2, wherein the inhibitor is in an orally-dosable form.

4. A platelet aggregation inhibitor according to claim 2, wherein the inhibitor is in a parenterally-dosable form.

* * * * *